United States Patent [19]
Sarhaddar et al.

[11] Patent Number: 5,641,406
[45] Date of Patent: Jun. 24, 1997

[54] LACTIC ACID EXTRACTION AND PURIFICATION PROCESS

[75] Inventors: Schahroch Sarhaddar; Anton Scheibl, both of Vienna; Emmerich Berghofer, Pressbaum; Adalbert Cramer, Roitham, all of Austria

[73] Assignee: Vogelbusch Gesellschaft m.b.H., Vienna, Austria

[21] Appl. No.: 505,166

[22] PCT Filed: Feb. 17, 1994

[86] PCT No.: PCT/AT94/00016

§ 371 Date: Oct. 10, 1995

§ 102(e) Date: Oct. 10, 1995

[87] PCT Pub. No.: WO94/19307

PCT Pub. Date: Sep. 1, 1994

[30] Foreign Application Priority Data

Feb. 18, 1993 [AT] Austria ............................ 310/93

[51] Int. Cl.⁶ ............................................ B01D 15/08
[52] U.S. Cl. ................ 210/656; 210/659; 210/198.2; 435/139; 562/580; 562/589
[58] Field of Search ............................ 210/635, 656, 210/659, 198.2; 435/139; 562/580, 589

[56] References Cited

U.S. PATENT DOCUMENTS

| | | | |
|---|---|---|---|
| 4,288,619 | 9/1981 | Devos | 210/198.2 |
| 4,814,273 | 3/1989 | Brumm | 435/139 |
| 5,068,418 | 11/1991 | Kulprathipanja | 562/580 |
| 5,068,419 | 11/1991 | Kulprathipanja | 562/580 |
| 5,143,834 | 9/1992 | Glassner | 435/145 |
| 5,245,078 | 9/1993 | Maeda | 562/580 |
| 5,472,616 | 12/1995 | Szmanda | 210/683 |

FOREIGN PATENT DOCUMENTS

| | | | |
|---|---|---|---|
| 878531 | 2/1980 | Belgium | 210/198.2 |
| 2455022 | 11/1980 | France | 210/198.2 |

OTHER PUBLICATIONS

Chem Abstracts vol. 78, No. 21,No.1 135586b,May 28, 1973.

Pat. Abstracts of Japan vol. 12, No. 110 (c–486) Apr. 8, 1988.

Chem Abstracts vol. 111, No. 9,No. 76533b, Aug. 28, 1989.

*Primary Examiner*—Ernest G. Therkorn
*Attorney, Agent, or Firm*—Henry M. Feiereisen

[57] ABSTRACT

The subject of the invention is a process for extracting pure lactic acid from fermentation liquors by ion exchange chromatography on a strongly acidic cation exchanger, preferably in $H^+$ form. In a first step, the $NH_4$ lactate coming from the fermentation is converted into the free acid by genuine ion exchange. This conversion is preferably effected on a weakly acidic cation exchanger in $H^+$ form.

15 Claims, 9 Drawing Sheets

LACTIC ACID EXTRACTION AND PURIFICATION PROCESS

BACKGROUND OF THE INVENTION

The invention is directed to a process for the separation and purification of lactic acid from salt-containing and carbohydrate-containing substrates (fermentation solution) from which coarsely dispersed and lipophilic impurities have been removed.

Industrial production of lactic acids, especially where pure L(+)-lactic acid and D(−)-lactic acid are to be extracted, is presently carried out predominantly by biotechnological processes. The production process can be divided into:

1) the actual production of lactic acid by fermentation of a carbohydrate-containing medium;

2) the working up (downstream processing) of the fermentation solution to form pure acid.

Industry has adopted a large number of strains of microorganisms for the production of lactic acid. The most important of these are the homofermentative lactic acid bacteria of the genera *lactobacillus, streptococcus* and *pediococcus*. However, these genera reach their maximum productivity only within a very narrow pH range.

Therefore, it is necessary during fermentation not only to maintain a constant optimum temperature for the selected organism, but also to maintain the required pH at a constant value. For this reason, neutralizing agents such as alkali hydroxide, calcium carbonate, milk of lime or ammonia water are added to the mash before and/or during fermentation so as to prevent over-acidification and to maintain a constant pH of 5.5 to 6.5.

Thus, the main component contained in the fermentation mash is the salt of lactic acid (e.g., $NH_4$ lactate or Ca lactate) in addition to a little free acid, as well as unconverted starter materials (e.g., sugar), heavy metals, coloring matter, metabolic by-products (e.g., acetic or ethanoic acid), cells and cell fragments of the microorganisms, and inorganic salts.

Therefore, direct use of the solution coming from fermentation is not possible and further processing steps are required to extract the pure, free lactic acid.

A number of methods are described for the separation and extraction of free lactic acid from the fermentation mash.

The simplest commercial method of purification, and that most often applied by manufacturers, is precipitation of the lactic acid as calcium lactate. In this method, at the end of the fermentation process the mash is first heated to approximately 80°–90° C. and the pH is increased to 10–11. In this step, the microorganisms are destroyed, the proteins are coagulated and the formed calcium lactate is dissolved. After all insoluble components have been separated, the mash is acidified with sulfuric acid to liberate the lactic acid from its salt. In order to remove the iron and copper ions introduced especially as a result of corrosion, as well, sodium hexacyanoferrate (II) or calcium hexacyanoferrate (II) is added and the precipitated ferrocyanide salts, together with the calcium sulfate, are separated by means of a rotary filter or filter press. Coloring components are removed by activated charcoal. The obtained dilute acid is then concentrated to lactic acid of approximately 80% strength, small amounts of resulting volatile acids being removed at the same time.

In improved precipitation processes, the crude lactic acid is first decolorized with activated charcoal and subsequent purification steps can be carried out by means of cation exchangers for complete removal of any remaining salts. The cation-free solution can then be evaporated or crystallized immediately or can be guided through an anion exchanger in order to remove any remaining foreign anions, mainly sulfate ions and chloride ions (DD-PS 6740).

For a further improvement in quality, especially with respect to odor and flavor, an oxidative treatment with hydrogen peroxide or potassium permanganate is frequently also carried out subsequently (CARLOS BELLAPART VILA, 1964, ES 297969).

However, all precipitation methods have grave disadvantages. Apart from the relatively high technical costs, the primary disadvantage consists in a material loss of up to 20% of the lactic acid due to the precipitation and crystallization processes (HEDING, L. G., Biotechm. Bioeng. 17, 1975, 1363–1364). Moreover, these methods require large quantities of auxiliary chemicals. Since the lactic acid occurs in most cases as calcium lactate which must first be converted to free acid with sulfuric acid and an equivalent amount of gypsum or calcium sulfate, the costs for disposing of large amounts of calcium sulfate are added to the cost for lime and sulfuric acid.

The grade of lactic acid which can be produced by this "precipitation method" is edible-grade lactic acid and is accordingly only suitable for the foodstuffs industry. However, the pharmaceutical industry requires lactic acid of higher purity. Even higher criteria for purity are required for plastics produced from lactic acid by polymerization. In particular, this requires a total absence of carbohydrates. Therefore, there has been no lack of attempts to find other methods for extracting the lactic acid from the fermentation solution in order to produce higher grades of lactic acid (pharmaceutical-grade lactic acid, plastic-grade lactic acid).

One possibility for producing pharmaceutical-grade lactic acid is steam distillation with superheated steam under vacuum. Lactic acid, as is well-known, has a very low volatility with steam at 100° C. However, the steam volatility can be considerably increased by using superheated steam in a temperature range of 160°–200° C. Based on these results, methods for purification of lactic acid by steam distillation have been worked out, e.g., as described in patents DK 83589 (1957) or CS 97136 (1960). However, this method—by far the oldest—for production of pharmaceutical-grade lactic acid has not been successful in practice since this purification process is much too costly due to the relative "nonvolatility" of the lactic acid.

Liquid-liquid extraction of lactic acid with organic solvents, however, has been more successful. In principle, the procedure in this method consists in that the fermentation solution which has been freed of biological matter is acidified with sulfuric acid, the precipitated calcium sulfate is removed by filtration and, finally, decolorizing is carried out with activated charcoal and salts are removed by ion exchange. The crude lactic acid solution produced in this way is then concentrated under vacuum to a determined concentration and is brought into contact with an organic solvent in a countercurrent extraction column. The lactic acid can then be extracted from the organic phase either by backextraction with water or by distilling off the organic solvent. Further treatment of the pure lactic acid solution with activated charcoal and ion exchangers is often required after the extraction process before it can be concentrated to the conventional commercial concentration of 80%.

A process of this kind is described, e.g., by JENEMANN (1933) in U.S. Pat. No. 1,906,068, where isopropyl ether is used as a solvent.

An extraction process using nitroparaffin as the organic phase is proposed in TINDALL (1940), U.S. Pat. No. 2,223,797.

Also, in more recent times there has been no shortage of attempts to improve the process for obtaining lactic acid by extraction.

For example, DE-OS 3415141 proposes an extraction process in which butanols or pentanols are used as solvents. The characteristic feature in this method consists in that the liquor containing calcium lactate is acidified with sulfuric acid immediately after fermentation and the obtained suspension which contains calcium sulfate and biomass as solids is brought into contact with the solvent directly in a pulsed countercurrent column outfitted with built-in hydrophobic pieces (e.g., made of Teflon). After the extraction of the aqueous suspension by the solvent, which is preferably carried out at a temperature of 70° C., a solids-containing aqueous phase and a solids-free organic phase are removed from the column. The lactic acid dissolved in the organic phase is finally converted completely into the lactic acid ester by distilling the reaction water at 60°–140° C. (possibly under vacuum). This lactic acid ester can be obtained in pure form by vacuum distillation and is a valuable intermediate product. The esters can be split again into lactic acid and alcohol, as is well-known, so that highly pure pharmaceutical-grade lactic acid can be obtained.

A great disadvantage in all extraction methods consists in that most of the organic solvents used for lactic acid have only a very low distribution coefficient so that very large quantities of organic solvents are required.

However, the distribution coefficient for lactic acid can be substantially improved when a mixture of organic solvents with a tertiary amine is used for extraction. A purification process based on this principle is described, for example, in U.S. Pat. No. 4,698,303 (1987) in which a mixture of approximately 60%–75% isobutyl heptyl ketone and 25%–40% Adogen 364 was proven especially effective as an extraction medium. Adogen 364 is the trade name (Sherex Co.) of a mixture of long-chain (C8–C10) tertiary amines.

However, certain difficulties arise in this purification process in recovering the lactic acid from the organic phase, since this can only be carried out by backextraction with a basic solution (preferably ammonium hydroxide). This means that additional purification steps are required after extraction.

Although the lactic acid obtained by liquid-liquid extraction is substantially free of ash, it does contain other impurities stemming from the raw material. Very pure starter mashes as well as additional treatments, e.g., with activated charcoal, oxidizing agents and ion exchangers, are required to obtain pharmaceutical-grade lactic acid by this method (VICKROY, T. B., Lactic Acid in. Comprehensive Biotechnology, Vol. 3, 761–776, Pergamon Press) (PECKHAM, G. T., 1944, Chem. Eng. News, 22, 440–443).

Therefore, the method most frequently applied for the production of pharmacopeia lactic acid is esterification of the lactic acid with low alcohols (usually methanol) and subsequent separation of the esters by fractional distillation. Numerous methods for the purification of lactic acid by esterification are described in the literature. In a part of this process the crude lactic acid which is reduced to a determined concentration, and to which is generally added an acid catalyst, is exposed to the action of alcohol vapors. For the most part, lactic acid is separated from the escaping vapor mixture as esters of the accompanying substances. The surplus alcohol is separated and fed back in a subsequent rectifying column. The methyl lactate can finally be hydrolyzed again with water to form methanol and lactic acid.

The esterifying reaction of concentrated lactic acid with methanol in the presence of an acid catalyst does not present any difficulties with respect to purification. Thus, DE-OS 1912730 describes a process for the production of lactic acid methyl ester in the presence of an acidic ion exchanger, wherein the ester is obtained in a yield of 82 percent by fractional vacuum distillation.

Purification of the esters becomes more difficult when starting from a diluted aqueous lactic acid solution because the ester can be hydrolyzed again very easily in the presence of water. In U.S. Pat No. 2,350,370, although diluted aqueous lactic acid is esterified with an acid catalyst, the distilled ester is saponified again immediately in order to purify the lactic acid.

DE-OS 3214697 proposes a process for continuous purification of lactic acid methyl esters in which the ester, which is produced by esterification of a diluted lactic acid with an acid catalyst, is first concentrated by partial condensation of the gas mixture occurring during esterification and by subsequent vacuum distillation, and the crude lactic acid methyl ester remaining in the sump or bottom of the first separation column which contains only essentially small amounts of lactic acid is guided into a second separation column for complete purification.

Even though the "esterification method" is currently the only usable method for producing pharmacopeia-grade lactic acid, it still has the disadvantage that large amounts of organic solvent must also be used, which poses a considerable safety hazard and risk to the environment.

For this reason there was an intensification of the search for alternative methods not having the disadvantages mentioned above.

Thus, a number of patents are known which propose that the organic acids be separated by electrodialysis. AT 290441, for example, proposes a process for purification of lactic acid in which a lactic acid which is free from "unpleasant odor and taste" is obtained by a combination of electrodialysis and extraction. In this process, a crude lactic acid solution which has been concentrated to approximately 20% is subjected to electrodialysis treatment and the dialyzed solution is then extracted with an organic solvent (isopropyl ether is recommended). The lactic acid is obtained from the organic phase by backextraction with water.

A process for purifying lactic acid is suggested in EP 0393818, in which the lactic acid salt (e.g., $NH_4$ lactate) contained in the fermentation liquor is first separated by conventional electrodialysis. The lactic acid salt extracted in this way is then directed to a second electrodialyzer which is outfitted with bipolar membranes and in which the lactic acid salt is separated into the free acid and its corresponding base by hydrolysis. Finally, the lactic acid solution is guided through a strongly basic and a strongly acidic ion exchange resin in order to remove any anions and cations which may be present. A lactic acid of high purity is obtained in this way.

However, processes using electrodialysis have the disadvantage that they require large amounts of electrical energy on the one hand, which renders the process very expensive, and additional purification steps, e.g., ion exchange, on the other hand in order to produce highly pure lactic acid.

Another alternative method for extracting and/or purifying carboxylic acids produced by fermentation is the ion exchange method with acidic and/or basic ion exchange resins.

DD-PS 203533 describes an ion exchange process for extracting carboxylic acids and hydroxycarboxylic acids from their solutions containing foreign salts, in which the salts are first transformed into acids via strongly acidic cation exchangers in $H^+$ form. In so doing, a mixture of carboxylic acids and foreign acids is obtained. A weakly basic anion exchanger which is first present in the form of a base or hydroxyl is loaded with a small concentrated fraction of this mixture, i.e., substantially converted to the form of carboxylic acid. Next, a more highly concentrated fraction of the acid mixture obtained in the decationization step is guided via the acid-charged ion exchanger. The acid to be extracted passes freely through the resin bed and only the stronger foreign anions (chloride is mentioned) bind to the resin by ion exchange.

EP 0135728 describes a process for "isolating enzymatically produced carboxylic acids" in which the solution which is advantageously produced by continuous fermentation runs through a "desorber" filled with a "polymer with tertiary amino groups" which selectively adsorbs carboxylic acids. The liquid exiting from the "desorber" which is extensively free of carboxylic acids is guided back into the reactor again. After exhausting a "desorber", the reaction solution is guided to the next desorber and the carboxylic acid is eluted from the exhausted desorber by means of a polar solvent, e.g., methanol. The separation of the carboxylic acid from the eluate is carried out by known methods, e.g., by distillation in the case of volatile eluting agents.

Other processes for separating lactic acid by ion exchange are suggested in U.S. Pat. No. 3,202,705 and JP 91183487. In these processes, after separation of the precipitated $CaSO_4$, the fermentation liquor which is acidified with sulfuric acid is first guided through a strongly acidic cation exchanger in $H^+$ form and then through a basic anion exchanger. In this way, a "colorstable" lactic acid is obtained, at least in the U.S. patent.

The great disadvantage in all methods in which a "genuine" ion exchange takes place is the required cost for regenerating the resins.

Therefore, chromatography processes on basic anion exchangers are described as the most up-to-date alternative method for extracting and purifying organic acids.

For example, EP 0324210 proposes a purification process in which a citric acid produced by fermentation is purified by adsorption at neutral, nonionic, macroreticular, water-insoluble resins or at weakly or strongly basic anion exchangers. Water, a mixture of water and acetone, or a diluted sulfuric acid solution are used as eluent. This method is capable of separating salts and carbohydrates from the citric acid.

The process proposed in EP-OS 0377430 works on precisely the same principle. In this method, basic ion exchangers are also suggested for chromatographic isolation and/or purification of acids. The chief difference compared to EP 0 324 210 consists in that this method can be used to separate and/or purify not only citric acid, but also other inorganic acids (e.g., phosphoric acid) and organic acids (tartaric acid, malic acid or lactic acid).

However, all ion exchange chromatography or IEC methods using basic anion exchangers or nonionic adsorber resins have the great disadvantage that the acids retained on the resin by adsorption show a high degree of "tailing" when eluted with water or with diluted sulfuric acid, which results in an intensive dilution of the eluted acid. Further, it is impossible with this method to separate acids having similar pKs values, e.g., lactic acid and ethanoic acid.

SUMMARY OF THE INVENTION

The object of the present invention is to extract lactic acid from salt- and carbohydrate-containing substrates (fermentation mashes) in a simple and reliable manner.

This object is met, according to the invention, in that the separation and purification process is carried out in two steps:

a) in the first step, the salts which may be present in the fermentation solution, principally the salt of lactic acid, are converted into free acids by means of genuine ion exchange in one or more "preliminary columns", and b) in the second step, the free lactic acid is separated from the rest of the acids, carbohydrates and other impurities present in the fermentation solution by chromatography at strongly acidic ion exchangers in one or more "separation columns".

This process provides the following advantages:

The fermentation mash need not be mixed with a strong mineral acid to liberate the lactic acid, which considerably reduces the salt contents of the mash. Compared with methods in which strongly acidic cation exchangers are used to separate the lactic acid from the usually acidified liquor by classic ion exchange, the chief advantage consists in that the amount of mineral acid required for regenerating a weakly acidic ion exchanger is reduced by roughly two thirds.

The advantage compared with IEC methods with basic anion exchangers consists in that the lactic acid fraction is obtained as a sharp symmetrical peak without "tailing".

Further, the separation of lactic acid from other present organic acids, in particular ethanoic acid, is also possible on strongly acidic ion exchangers. Accordingly, pharmaceutical-grade lactic acid with sufficient color stability can be obtained so that it can also be used for polymerization.

In contrast to IEC methods with basic exchangers requiring diluted acids for elution, pure water can be used as eluting agent in the present process.

The fermentation solution from which the lactic acid is to be separated must have a pH greater than 5.0 and accordingly still lies within the working range of strongly acidic cation exchangers.

The resin located in one or more "preliminary columns" is a cation exchanger, preferably a weakly acidic cation exchanger in $H^+$ form, since this enables regeneration into $H^+$ form with practically theoretical yields of acid (FIG. 7).

The temperature of the "preliminary column" should be at least 50° C., but preferably 70°–80° C., since this increases the acidity and accordingly also the salt separation capacity of weakly acidic cation exchangers and substantially improves the useful capacity (break-point or breakthrough capacity) of the exchanger.

The strongly acidic cation exchanger found in one or more "separation columns" is present in $H^+$ form so that a chromatographic separation of the lactic acid from other organic acids, in particular ethanoic acid, is also possible.

Upon contact with the strongly acidic cation exchanger, the decationized fermentation solution is divided into a raffinate fraction I (initial fraction) containing the components without a lactic acid content, a product fraction containing lactic acid, and a raffinate fraction II (final fraction) containing primarily ethanoic acid.

Pure, preferably deionized, water is used as eluting agent for washing the individual fractions out of the separation columns.

The elution temperature lies between room temperature and the stability threshold temperature of the resins employed, preferably between 50° C. and 65° C., so as to prevent microbial infection and increase the number of theoretical plates.

Only the weakly acidic cation exchanger located in the "preliminary columns" is regenerated with a diluted strong mineral acid, preferably a 1–2N sulfuric acid, after being completely loaded by the cations of the fermentation solution.

The diluted salt solution occurring in the regeneration of the resins in the preliminary columns is separated into the corresponding acids and bases by salt-hydrolyzing electrodialysis and fed back to the process.

BRIEF DESCRIPTION OF THE DRAWING

The above and other objects, features and advantages of the present invention will now be described in more detail with reference to the accompanying drawing in which.

DETAILED DESCRIPTION OF PREFERRED EMBODIMENTS

Figure 1:
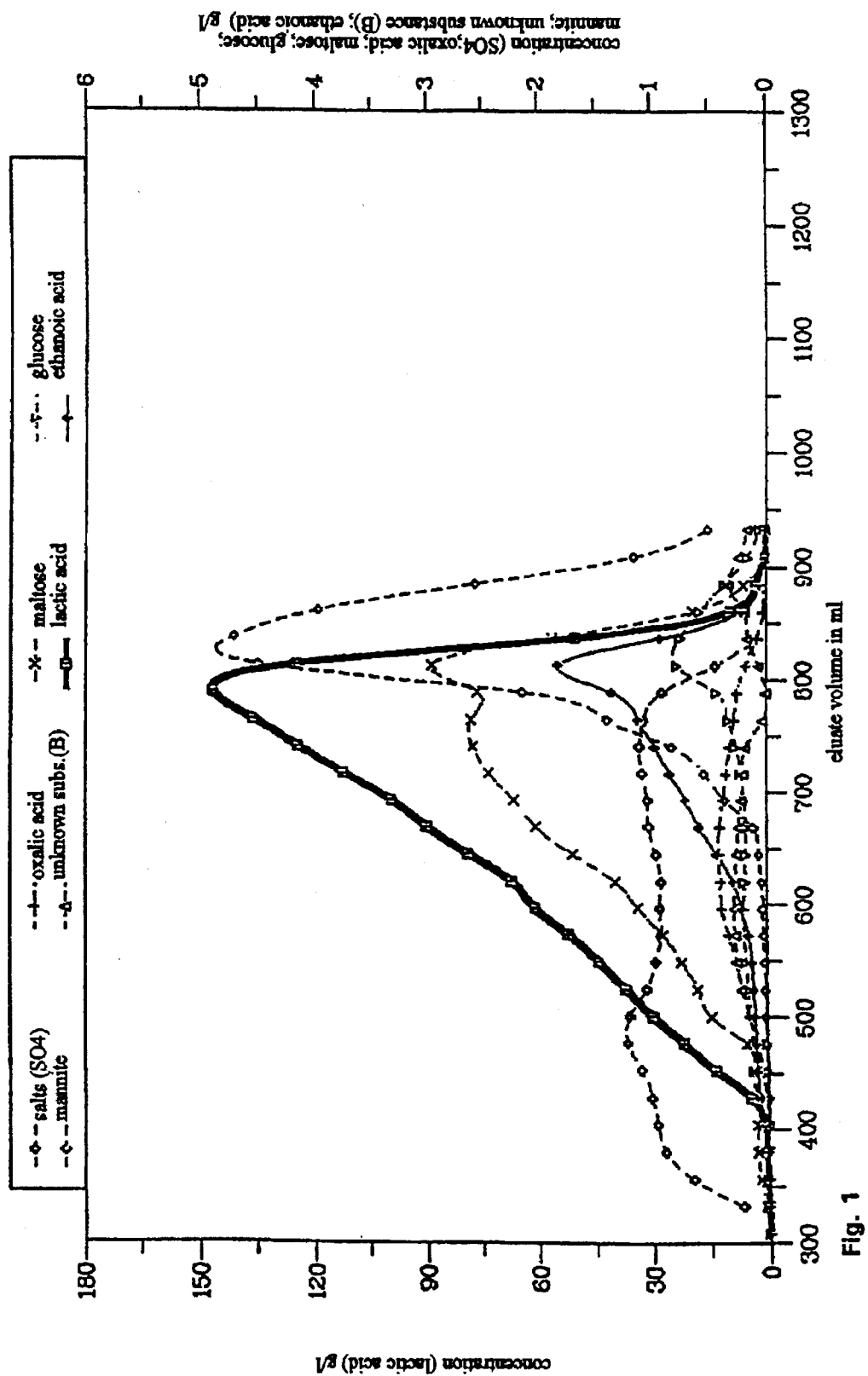
FIGS. 1 and 4 are graphical illustrations of IE chromatography of "feed" solution 1 with a strongly acidic cation exchanger.

More particularly, the process according to the invention is carried out in such a way that a lactic acid mash which is preferably produced by fermentation with *lactobacillus delbrueckii* with ammonia water as neutralizing agent is freed from coarsely dispersed components (biomass). This is effected, e.g., by centrifuging with a solid-jacket centrifuge. The fermentation solution may be mixed with activated charcoal to remove coloring matter and lipophilic components. After a period of contact, the activated charcoal is removed in conventional manner by filtration. The mash is concentrated, as the case may be, to 30–50% (w/w) by vacuum evaporation and provides the solution which is referred to hereinafter as "feed".

The actual purification and separation process of the lactic acid according to the invention is effected in two steps:

1) by a genuine ion exchange on a preferably weakly acidic cation exchanger in $H^+$ form, and 2) by an IE chromatography process on a strongly acidic cation exchanger in $H^+$ form.

The process begins by applying a determined volume of fermentation solution ("feed") to the "preliminary column". The amount of "feed" solution to be applied per chromatography cycle depends on its concentration and on the diameter of the "separation columns". In general, however, the amount lies between 5% and 10% of the resin bed volume of the "separation column".

When the "feed" solution has fully penetrated into the "preliminary column", pure, preferably deionized, water, the eluting agent used in this process, is switched to immediately.

A preferably weakly acidic cation exchanger in $H^+$ form is located in the "preliminary column". The salts contained in the "feed" solution, primarily the salt of lactic acid ($NH_4$ lactate), are converted into the corresponding acids by exchange of ions in this cation exchanger. The resin bed volume of the "preliminary column" need only be large enough so that, under the given operating conditions, the so-called "breakthrough capacity" of the resin used in the "preliminary column" is sufficient for the amount of cations applied per chromatography cycle to be exchanged with $H^+$ ions. Since the "breakthrough capacity" of weakly acidic exchangers depends not only on the pH of the "feed" solution but also, above all, on the operating temperature, it is advantageous to allow the ion exchange process in the "preliminary column" to take place at a temperature of at least 50° C., but preferably at 70°–80° C.

The decationized "feed" solution coming from the "preliminary column" is then conveyed via a pump directly to the "separation column" which is packed with a strongly acidic cation exchanger in $H^+$ form. The optimum flow rate required for the chromatography process is also maintained constant by means of the pump. The actual IEC process resulting in the separation of the lactic acid from the rest of the components in the "feed" solution takes place in the "separation column". The eluate flowing out of the "separation column" can be divided into three fractions:

\*) the raffinate fraction I (initial fraction) containing the components of the "feed" solution other than lactic acid (carbohydrates, strong acids, proteins)

\*) the product fraction containing the free lactic acid, and

\*) the raffinate fraction II (last fraction) containing primarily ethanoic acid.

The IEC process in the "separation columns" preferably takes place at a temperature of 50°–65° C. This prevents microbial infection of the resin and increases the number of theoretical plates.

The weakly acidic cation exchanger located in the "preliminary column" is regenerated with a strong mineral acid (e.g., with a 1–2N sulfuric acid) by the countercurrent method after being loaded by the cations of the "feed" solution. The diluted saline solution which occurs during regeneration of the "preliminary column" and which is principally composed of ammonium sulfate, can be separated by salt-hydrolyzing electrodialysis into the corresponding acids (sulfuric acid) and bases (ammonium hydroxide) and fed back into the process.

As was already mentioned, the optimum pH value for the microorganism must be maintained constant during the fermentation of the lactic acid in order to achieve satisfactory productivity. This is effected in a simple manner by adding a neutralizing agent such as $NH_4OH$ to the mash during fermentation so that the pH of the solution is held constant at 5.5–6.5. Thus, in addition to small amounts of salts, carbohydrates and other impurities stemming from the nutrients, the mash coming out of the fermentation contains the salt of lactic acid, e.g., $NH_4$ lactate, as the main component.

A number of effects come into play in chromatographic separation of multicomponent systems such as the lactic acid mash described above.

The first effect is the "ion exclusion effect" described by WHEATON and BAUMANN (1953) (Ing. Eng. Chem.; 45 (1953) 228). This enables the separation of ionic and nonionic components. In this case, as opposed to the conventional ion exchange process, there is no exchange of ions, so that regeneration of the resin is also not required. The theory of the ion exclusion effect can be explained and described by the "Donnan membrane theory" (MEYER, W. R. S., et al.; Ind. Eng. Chem. Proc. Des. Develop.; 6 (1967) 55). For example, if a salt solution $K^+A$ is brought together with a cation exchange resin which has been saturated beforehand by the cation $K^+$, the resin takes on a negative charge in relation to the solution. This negative charge is the result of a slight traveling of the anion A in the resin and a similar traveling of the cation $K^+$ in the intermediate space of the resin. A potential difference develops between the solution and the resin phase. The magnitude of this potential difference can be described by the Donnan membrane potential.

For practical applications this means that dissolved salts which, as cations, contain the same ion as the counter-ion of the resin cannot penetrate into the resin and will be the first component to exit the column. The same principle applies also to acids to be separated on a strongly acidic cation exchanger in $H^+$ form. However, in the case of acids, the pKs value of the acid in question still plays a part. The lower the pKs of the acid (i.e., the stronger the acid), the less the acid will be retained by the resin, and vice versa. This means that strong acids cannot penetrate into the resin pores due to Donnan exclusion, whereas medium-strong and weak acids, depending on their degree of dissociation, can penetrate to a varying extent into the resin pores and therefore exit the column only later on.

Another effect coming into play in IE chromatography is the so-called "molecular sieve effect" which is responsible for the separation of uncharged (nonionic) dissolved components (WALTER, H. G. et al., Cer. Sci. Today; 15 (1970) 140). The pore size of an ion exchange resin is determined by its degree of cross-linking. The size and shape of a molecule, as much as the pore size of the resin, determines whether a molecule can move from the intermediate space into the pore space when traveling through an ion exchange column. The ion exchanger acts as a molecular sieve which excludes molecules of a determined shape and size (NORMANN, L. G.; J. Amer. Soc. Sugar Beet Tech.; 12 (1963) 363). When eluting the column, those components which cannot move into the pores will appear in the eluate sooner than those which are uniformly distributed.

The so-called "distribution coefficient" ($K_{di}$) provides a yardstick for determining the degree to which a substance will be held back by the resin in question. It is defined as the ratio of the concentrations of the dissolved substance (i) in the resin pore volume ($C_{hi}$) to the concentration of the dissolved substance (i) in the intermediate space volume ($C_{zi}$):

$$K_{di} = C_{hi}/C_{zi}.$$

Very generally, the distribution coefficient for a determined compound depends on the structure of this compound and its concentration, on the type and ionic form of the resin and, finally, also on the other compounds present in the solution.

The chromatographic separation of lactic acid from a solution containing nonionic components (carbohydrates) in addition to ionic components (salts) is carried out on a strongly acidic cation exchanger by a combination of the two effects described above. However, a precondition for this consists in that there be no reversal of charge in the resin during the chromatography process, i.e., that the counter-ion of the cation exchanger must be the same as the cation most present in the solution in terms of quantity. For example, when the mash is neutralized with $NH_4OH$, this would be the $NH_4^+$ ion.

In a purely theoretical respect, a chromatographic separation of the $NH_4$ lactate from the rest of the components in the mash would have to be possible on a strongly acidic cation exchanger in $NH_4^+$ form. However, experiments have shown that a separation of the lactic acid salt with a cation exchanger in this charge form is only possible, if at all, with great difficulty, since the distribution coefficients of the individual components are not sufficiently different from one another in this resin form in the sense indicated above (Example 1, FIG. 1).

Moreover, a process such as this would not yield the free acids, but rather, naturally, the salt of the lactic acid, i.e., the $NH_4$ lactate, which would first have to be converted into the free acid in a subsequent step.

On the other hand, by carrying out the IEC process on a strongly acidic cation exchanger in $H^+$ form with a mash whose pH value has been decreased to 2.5 by a strong mineral acid (e.g., with concentrated $H_2SO_4$), a totally different chromatogram would result. The acids are displaced from their salts by acidifying the mash. The main components found in a solution of this kind are, aside from free lactic acid, primarily $(NH_4)_2SO_4$ and sulfuric acid. During chromatographic separation of this solution, the ammonium sulfate entering the separation resin along with the "feed" would lead to a partial charge reversal in the resin. The occurring sulfuric acid, along with the sulfuric acid which is present anyway in the "feed", will travel through the "separation column" most quickly in accordance with the "ion exclusion effect" and will also be the first component to exit the column. On the other hand, the lactic acid with a much weaker degree of dissociation (pKs 3.86) will travel more slowly through the separation column and, depending on its strength, will return a portion of the previously $NH_4^+$-charged resin into its $H^+$ form. The lactic acid appears as a double peak in the chromatogram, where the first peak shows the $NH_4$ lactate and the second peak shows the free lactic acid (Example 2, FIG. 2).

However, the double peak, that is, the division of the lactic acid present in the "feed" into a salt fraction and an acid fraction, can be prevented when a determined amount of preferably $2N\ H_2SO_4$ is fed immediately or at a determined interval after the charge of "feed" solution which is acidified to a pH of 2.5. The amount of sulfuric acid which must be fed in this way is determined by the $NH_4$ ion concentration of the "feed" solution. After the sulfuric acid is fed, elution is carried out, as is conventional, with deionized water. The free lactic acid appears as a sharp single peak in the chromatogram. The reason for this again is that the strong sulfuric acid travels through the separation resin much faster than the weaker lactic acid or than the much weaker ethanoic acid. The sulfuric acid charged after the "feed" solution will, as it were, "outrun" the lactic acid and other weak acids and will cancel the charge reversal of the resin into its $NH_4^+$ form caused by the ammonium sulfate (Example 3, FIG. 3).

A combination of ion exchange and IE chromatography already takes place in this process, albeit in the same column and in the same resin. However, the displacement of the lactic acid from its salt can also be effected directly by ion exchange on the separation resin. If a mash which is not acidified (pH 5.8) is applied as "feed" to a strongly acidic cation exchanger in $H^+$ form and followed in the same way as described above by a determined amount of sulfuric acid and is eluted with deionized water, the same chromatogram will result (Example 4, FIG. 4).

However, the process described above in which both "ion exchange" and "IE chromatography" take place on one and the same resin, a strongly acidic cation exchanger in $H^+$ form, has a decisive disadvantage. This consists in that the amount of sulfuric acid which must be fed after the "feed" solution cannot conceivably be sufficient in practice for a complete regeneration of the cation exchanger. In each cycle, a determined amount of $NH_4$ ions will remain on the exchanger. This means that the exchanger must be completely regenerated after a determined number of IEC cycles.

This disadvantage may be overcome in a simple manner by allowing the two processes, "ion exchange" and "IE chromatography", to run separately. For this purpose it is necessary that a "preliminary column" in which the cations in the "feed" solution are exchanged for $H^+$ ions by ion exchange is arranged upstream of the "separation column" which is packed with the strongly acidic cation exchanger in $H^+$ form and in which only the IEC process will take place. Therefore, this "preliminary column" is likewise packed with a cation exchanger in $H^+$ form which can have a strongly acidic as well as a weakly acidic character. However, since the pH value of the fermentation mash is greater than 5 and accordingly still lies in the working range of weakly acidic cation exchangers and has an acidity sufficient at least to hydrolyze the salt of a weak acid (lactic acid), it is advantageous in the process according to the invention to use weakly acidic cation exchangers in the "preliminary column". The resin bed volume of the "preliminary column" depends on the "feed" quantity applied per chromatography cycle and on the "breakthrough capacity" of the resin. Although weakly acidic cation exchangers have a very high total capacity (up to 4 val/l resin), their useful capacity (breakthrough capacity) is reduced by operating conditions. Aside from the pH value of the solution (insofar as it lies below 7 or lies between 7 and 4), the operating temperature has the greatest influence on the useful capacity of weakly acidic cation exchangers. Thus, the acidity and accordingly the salt-hydrolyzing capacity of the carboxylic acid resin, also relative to neutral salts, at first increases only slightly with increasing temperature, but increases very sharply above 50° C. Therefore, it is necessary to operate the "preliminary column" at the highest possible temperature, preferably 70° C.–80° C. (Examples 5 and 6, FIGS. 5 and 6).

Figure 5:
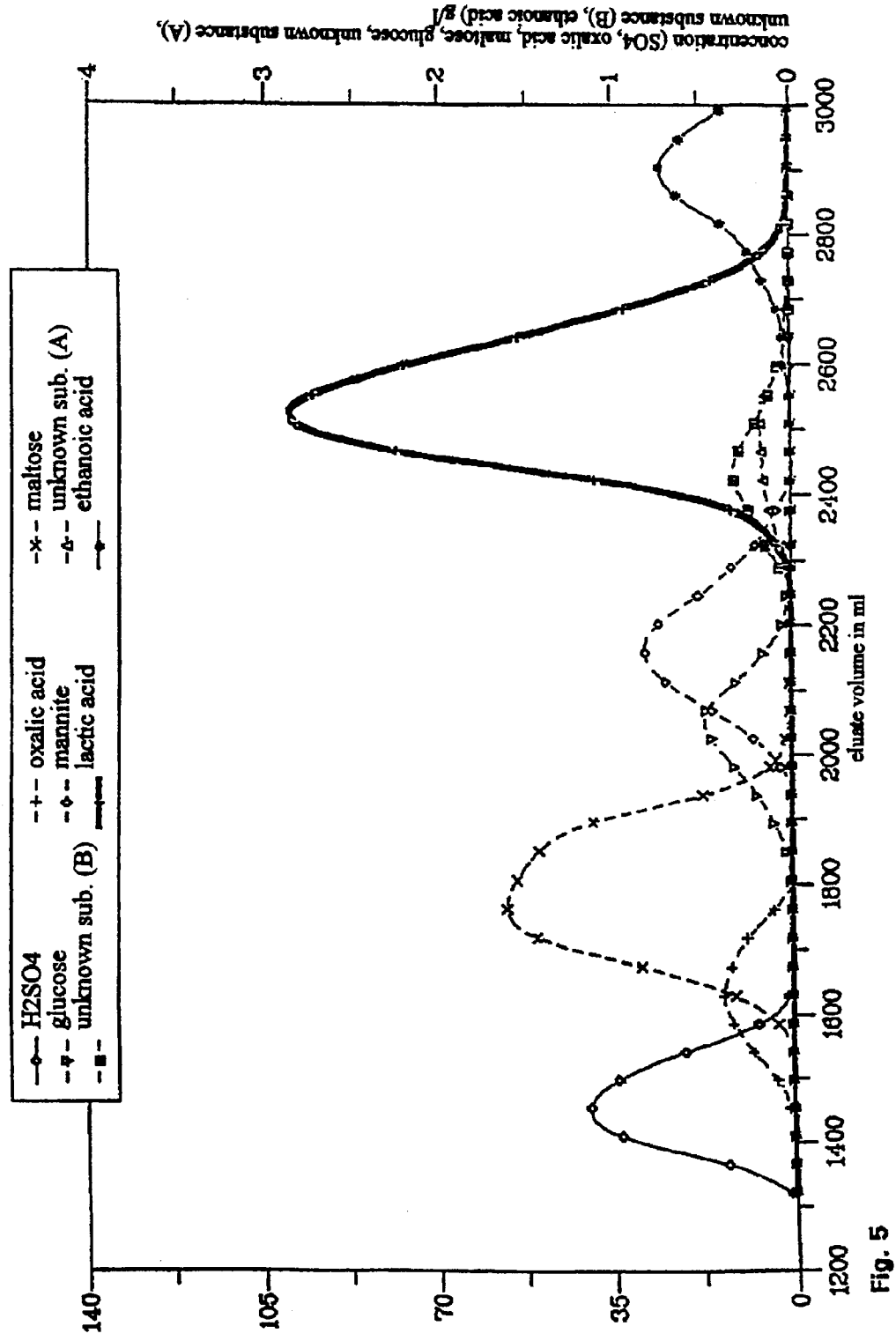
FIG. 5 is a graphical illustration of IE chromatography of "feed" solution 2 with a weakly and a strongly acidic cation exchanger.
Figure 6:
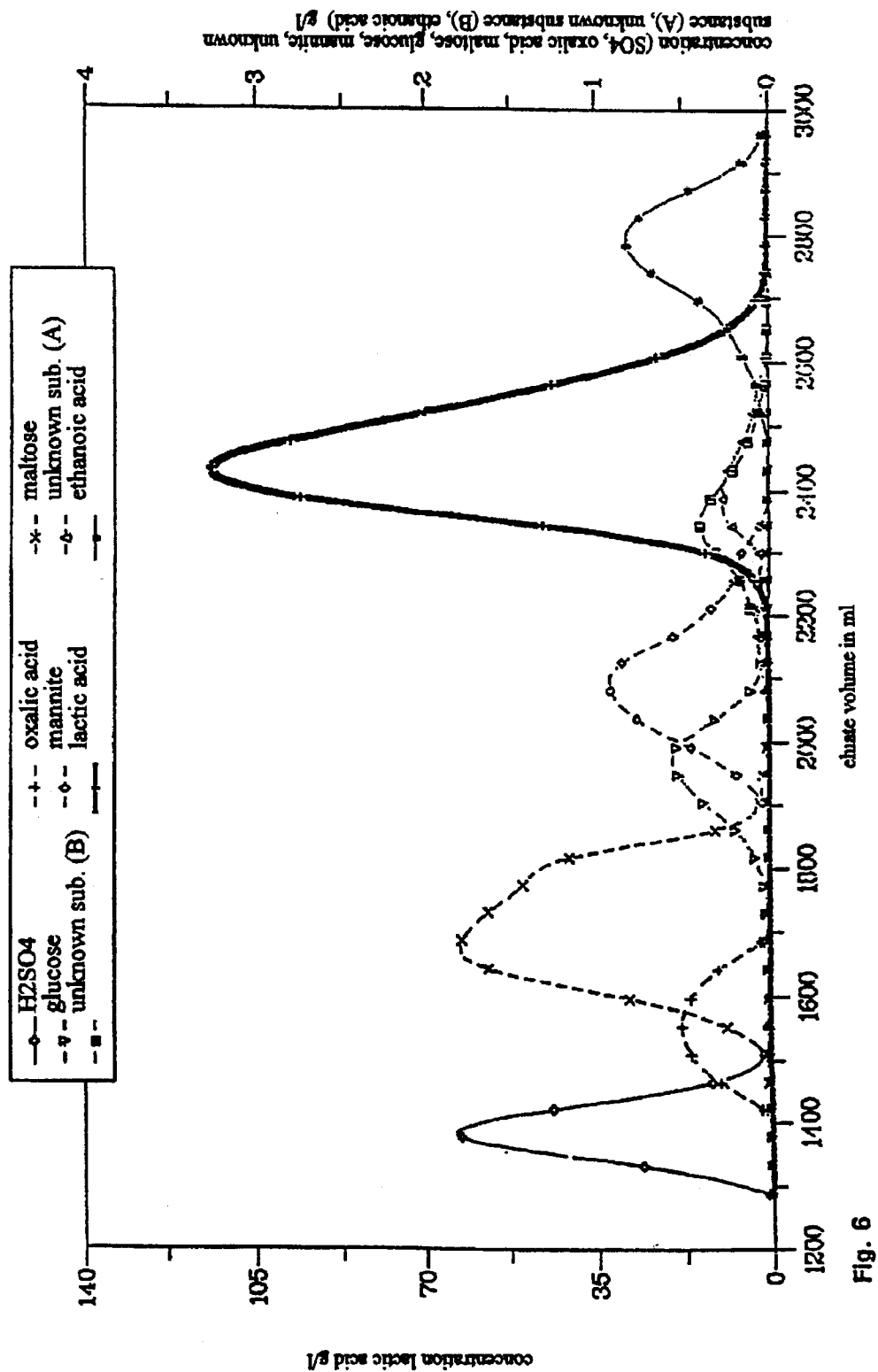
FIG. 6 is a graphical illustration of IE chromatography of "feed" solution 2 with two strongly acidic cation exchangers.

As will be seen from FIGS. 5 and 6, an extensive separation of lactic acid can be achieved already with the separating distance of roughly 800 cm available in the experimental facility. However, following the law of "theoretical plates", a complete separation of the lactic acid is to be expected with the separating distances of 15 to 20 m conventionally used in practice. Above all, a complete separation of carbohydrates from the lactic acid can be effected as is demonstrated in the "heat" test shown in Example 5, in which there was no discoloration after heating the lactic acid-containing fraction at 200° C. for one hour.

A decisive advantage of weakly acidic cation exchangers compared with strongly acidic cation exchangers consists in the high chemical utilization factor in regeneration. Due to the low dissociation constant, their regeneration into $H^+$ form can be carried out practically with the theoretical yield of acid (Examples 7 and 8, FIGS. 7 and 8).

Figure 9:
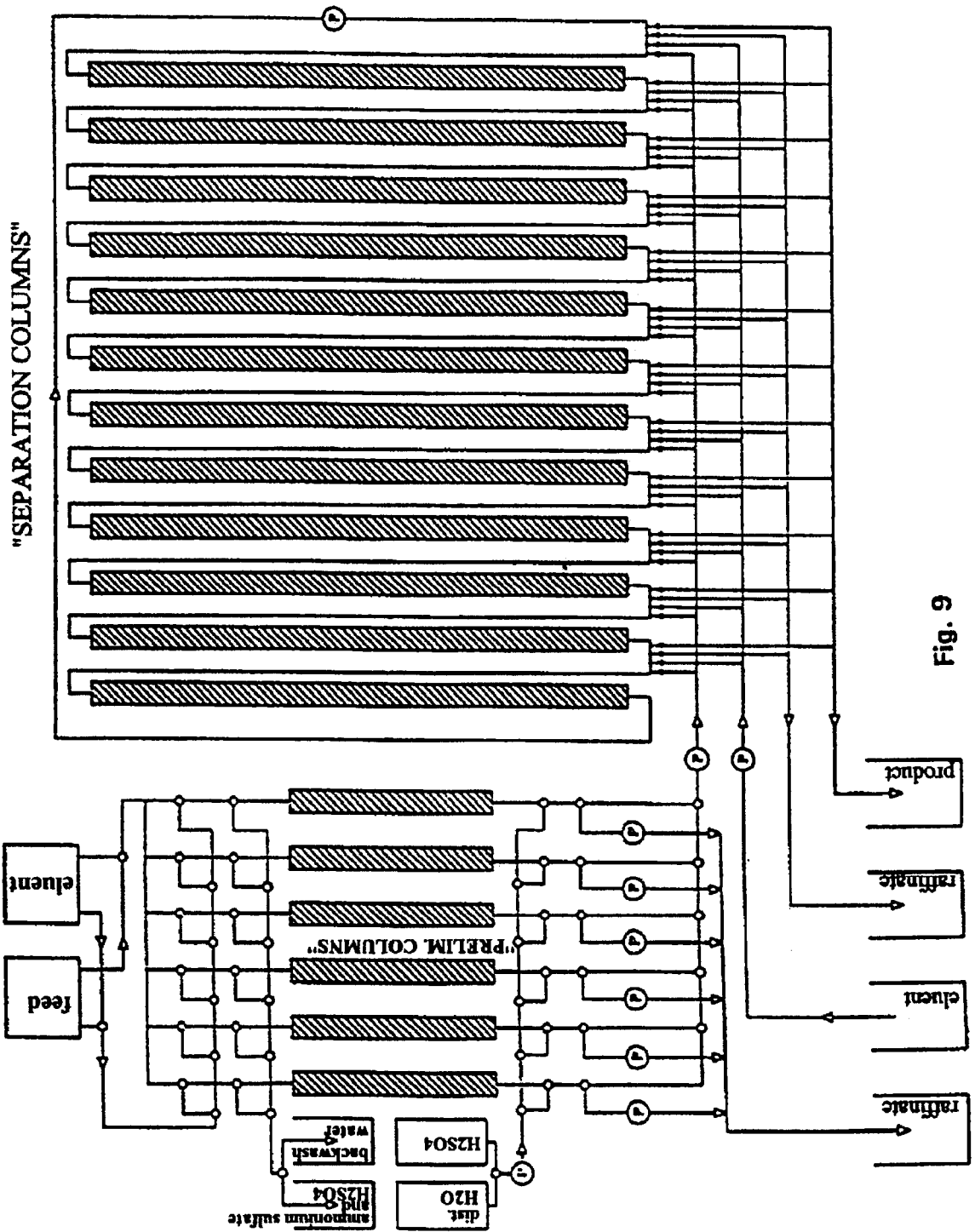
FIG. 9 shows a schematic view of a semicontinuous chromatography installation for extraction of pure lactic acid with "preliminary columns" and "separation columns" which are arranged and connected according to the principle of the "simulated moving bed" process.

The process described above can be realized in batch operation as well as in a quasi-continuous apparatus such as that described in the U.S. patent (1961). In this method, in the chromatography process described in the U.S. patent, the location at which the "feed" stream enters the separation resin and the location at which the "product" stream exits from the separation resin are constantly changed. This switching process simulates a double motion of the resin, for which reason it is referred to in the literature as the "simulated moving bed" process. A possible realization of this process incorporating the "preliminary columns" required for the process according to the invention is shown in FIG. 9, which shows a schematic view of a semicontinuous chromatography installation for extraction of pure lactic acid with "preliminary columns" and "separation columns" which are arranged and connected according to the principle of the "simulated moving bed" process.

In principle, the separation process and purification process are carried out in this installation precisely as described in the preceding, with the exception that semicontinuous operation can be carried out in this case. Here, also, a determined "feed" amount is applied to one of the "preliminary columns" and is rinsed down with water. After a certain period, an additional "feed" amount is applied to the next "preliminary column", thus producing a continuous "feed" stream. The decationized "feed" coming from the "preliminary column" is conveyed directly to a determined "separation column" by a pump (P), while the resin in this "preliminary column" is regenerated with sulfuric acid. This cyclical loading and regeneration of the "preliminary columns" can be repeated as often as desired.

The "separation columns", on the other hand, are connected via a pipeline to form a ring. This ring line is connected between the columns via valves to four supply lines. These supply lines enable four process flows:

\*) the "feed" inlet flow
\*) the "eluent" inlet flow
\*) the "product" outlet flow
\*) the "raffinate" outlet flow.

The flow in the installation is maintained constant by an individual pump. In this process, there are always exactly four valves opened, these valves dividing the ring of columns into four zones:

The first zone is the so-called "adsorption zone" and lies between the point where the "feed" flow enters the "separation columns" and the point where the faster flowing substances are decanted as the "raffinate" flow.

The second zone is the so-called "purification zone" and lies between the point at which the "raffinate" flow exits the "separation columns" and the point where pure water enters the "separation columns" as "eluent" flow.

The third zone is the so-called "desorption zone" and lies between the point at which the "eluent" flow enters the "separation columns" and the point where the lactic acid is decanted as the "product" flow.

The ethanoic acid and other slow-running components (raffinate fraction II) are likewise decanted with the "product" flow, but are collected separately.

The fourth zone is the so-called "buffer zone" and lies between the point at which the "product" flow exits the "separation column" and the point where the "feed" flow re-enters the separation system.

At given times, these zones are switched one column farther in the flow direction by means of a process control computer. These switching processes simulate a resin flow in the opposite direction with respect to flow.

Compared to batch operation, the "simulated moving bed" process has the advantage that roughly one third less resin and roughly two thirds less eluent is needed for production of the same quantity of lactic acid.

The invention will be explained more fully in the following by examples. The resins used are common commercial products. Their general characteristics as specified by the manufacturer are compiled in Table 1:

TABLE 1

| feature | resin in preliminary columns | | resin in separation columns |
|---|---|---|---|
| | Dowex MWC-1 | Lewatit MDS 1368 | Dowex Mono C 356 CA |
| manufacturer | Dow Chemical | Bayer | Dow Chemical |
| resin type | weakly acidic | strongly acidic | strongly acidic |
| polymer base | polyacrylic macroporous | Styrene/DVB gel | Styrene/DVB gel |
| functional group | carboxyl group | sulfonic acid | sulfonic acid |
| particle size | 0.4–1.2 mm | 0.35 mm ± 0.05 | 0.35 mm ± 0.05 |
| moisture content | 44–50 % by wt. | approx. 49 % by wt. | 57–61 % by wt. |
| bulk density | 720 g/l | 830 g/l | 833 g/l |
| total capacity | 3.8 val/l | 1.8 val/l | 1.5 val/l |
| maximum operating temperature | 100° C. | 100° C. | 90° C. |
| pH working range | 5–14 | 1–14 | 1–14 |

The "feed" solution used in all IEC tests was a lactic acid mash produced by fermentation with *lactobacillus delbrueckii*. $NH_4OH$ was used as a neutralizing agent so that the lactic acid was present in the mash as ammonium lactate. After separation of the biomass by means of a chamber centrifuge, the mash was concentrated to approximately 30% wt./vol. by vacuum distillation and then decolorized by adding activated charcoal. The pH value in a portion of the mash produced in this way was reduced to 2.5 by the addition of concentrated sulfuric acid and the lactic acid was accordingly displaced from its salt.

The light-yellow solutions obtained in this way are designated in the following examples as "feed" solution 1 (pH 5.8) and "feed" solution 2 (pH 2.5).

Table 2 shows the composition of these solutions determined by high pressure liquid chromatography or HPLC (Shimadzu Co.):

TABLE 2 analytical characterization of the fermentation solution by HPLC

| substance | "feed" solution 1 fermentation solution at pH 5.8 | "feed" solution 2 fermentation solution at pH 2.5 |
|---|---|---|
| sulfate | 5.12 g/l | 124.20 g/l |
| oxalic acid | 1.07 g/l | 0.97 g/l |
| maltose | 4.68 g/l | 4.25 g/l |
| glucose | 1.99 g/l | 1.79 g/l |
| mannite | 4.64 g/l | 4.22 g/l |
| unknown substance A | 2.91 g/l | 2.62 g/l |
| unknown substance B | 2.28 g/l | 2.05 g/l |
| lactic acid | 303.93 g/l | 268.40 g/l |
| ethanoic acid | 2.80 g/l | 2.52 g/l |

EXAMPLE 1

A chromatography testing installation having two double-wall columns of acrylic glass in series was packed with the strongly acidic cation exchanger DOWEX Mono C 356 CA. The diameter of the inner column was 2.0 cm and the length of each column was 200 cm. At a resin bed height of 365 cm, this resulted in a resin bed volume of 1150 $cm^3$.

After the columns were packed with the resin, they were first brought to $H^+$ form with 2N HCl and then charged to $NH_4^+$ form with ammonia water (approx. 5%). All of the liquid volumes fed to the columns during the experiment were degassed beforehand and preheated to the column temperature. This temperature was 55° C. and was maintained constant by circulating thermostats.

After feeding 100 ml of the "feed" solution 1 to the first column, elution was carried out with degassed, deionized water which was preheated to approximately 60° C. The flow rate of 6 ml/min (1.91 ml/min*$cm^2$) was adjusted by a constricted-tube or peristaltic pump and maintained constant. The eluate exiting from the bottom of the first column was immediately pumped to the second column. The eluate of the second column was guided through a conductivity measurement cell and then collected in a fraction collector. The signal coming from the conductivity measurement cell was recorded by a plotter in the form of a conductivity chromatogram. This served only for rough detection, since only the position of the salts and acids can be detected by conductivity.

A more precise analysis of the collected fractions was carried out by HPLC. In this way the carbohydrates as well as the acids and salts could be determined quantitatively.

The concentrations of the individual substances determined by HPLC were plotted against the eluate volume and resulted in the chromatogram shown in FIG. 1.

EXAMPLE 2

Figure 2:
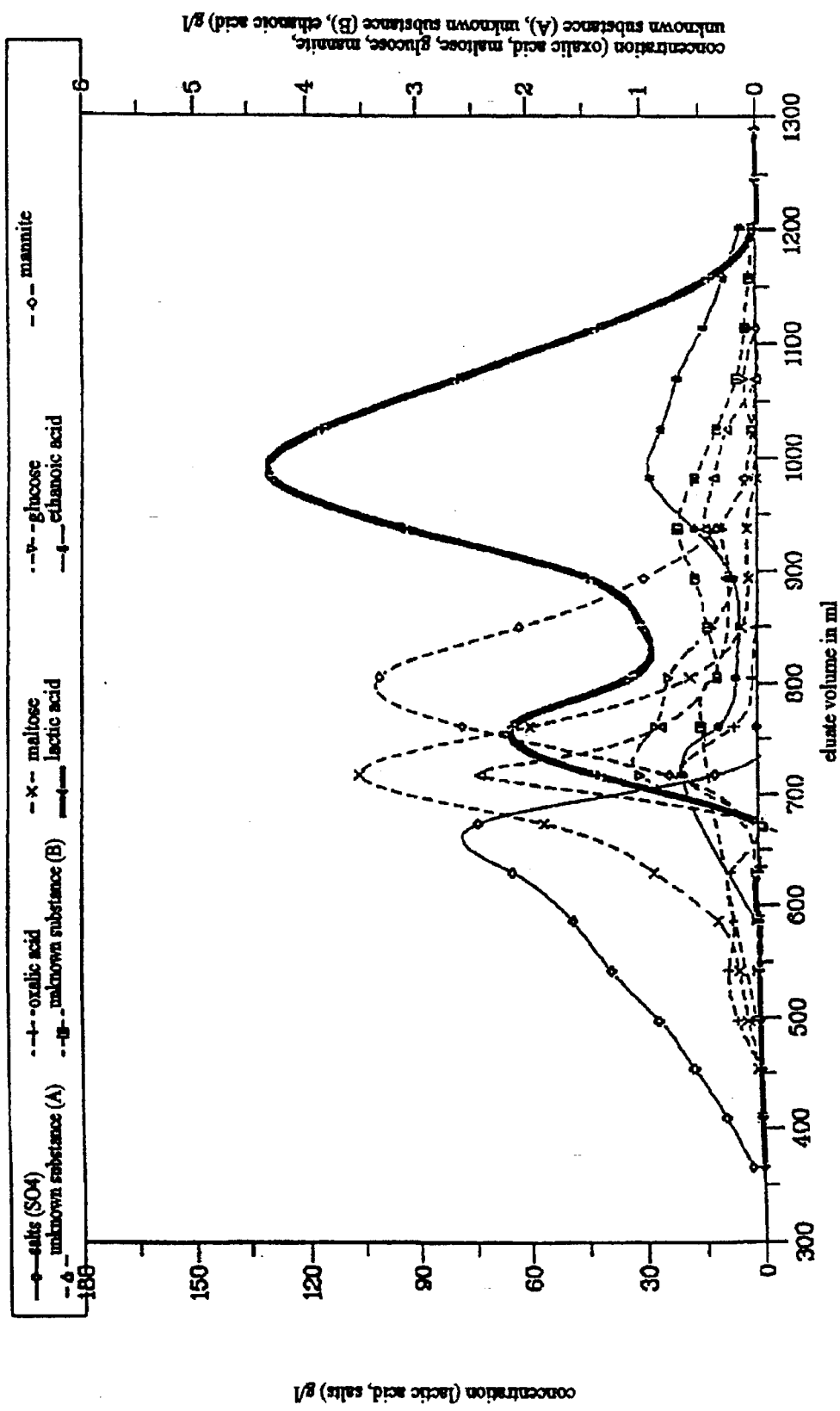
FIGS. 2 and 3 are graphical illustrations of IE chromatography of "feed" solution 2 with a strongly acidic cation exchanger.

The procedure was identical to Example 1, except that the strongly acidic cation exchanger was converted to $H^+$ form with 2N sulfuric acid and 100 ml of the "feed" solution 2 was applied to the resin. The chromatogram of this separation is shown in FIG. 2.

EXAMPLE 3

Figure 3:
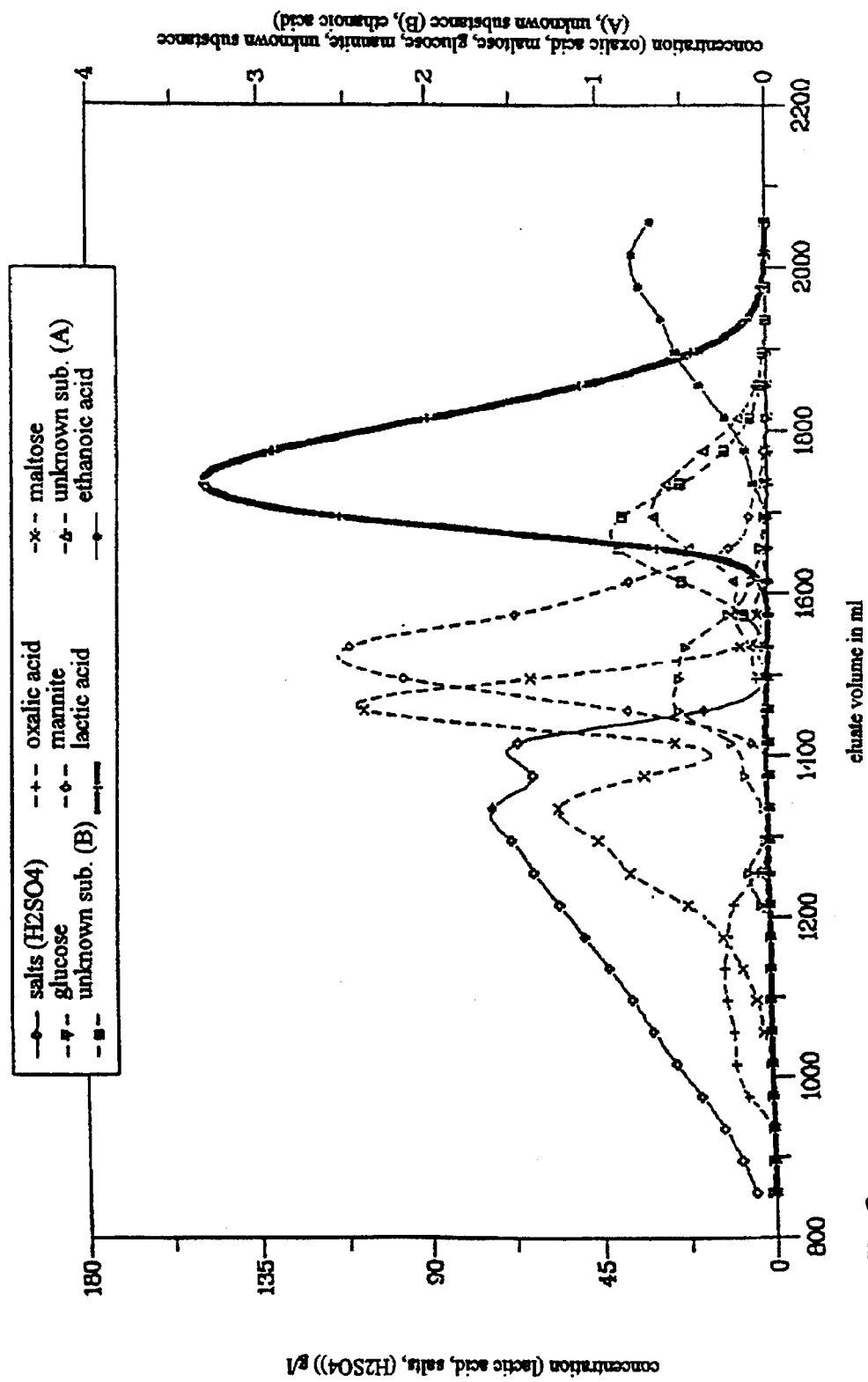

The procedure was identical to Example 2, except that the chromatography installation was supplemented by two additional columns so that a resin bed volume of approximately 2300 $cm^3$ resulted in a resin bed height of 730 cm. Only 60 ml of "feed" solution 2 was applied to the resin in this test. Elution was carried out such that 180 ml of 2N $H_2SO_4$ were supplied after rinsing the "feed" solution with 40 ml water in the resin bed. Next, water was switched to again and elution was brought to completion as described in Example 1. The chromatogram of this separation is shown in FIG. 3.

EXAMPLE 4

Figure 4:
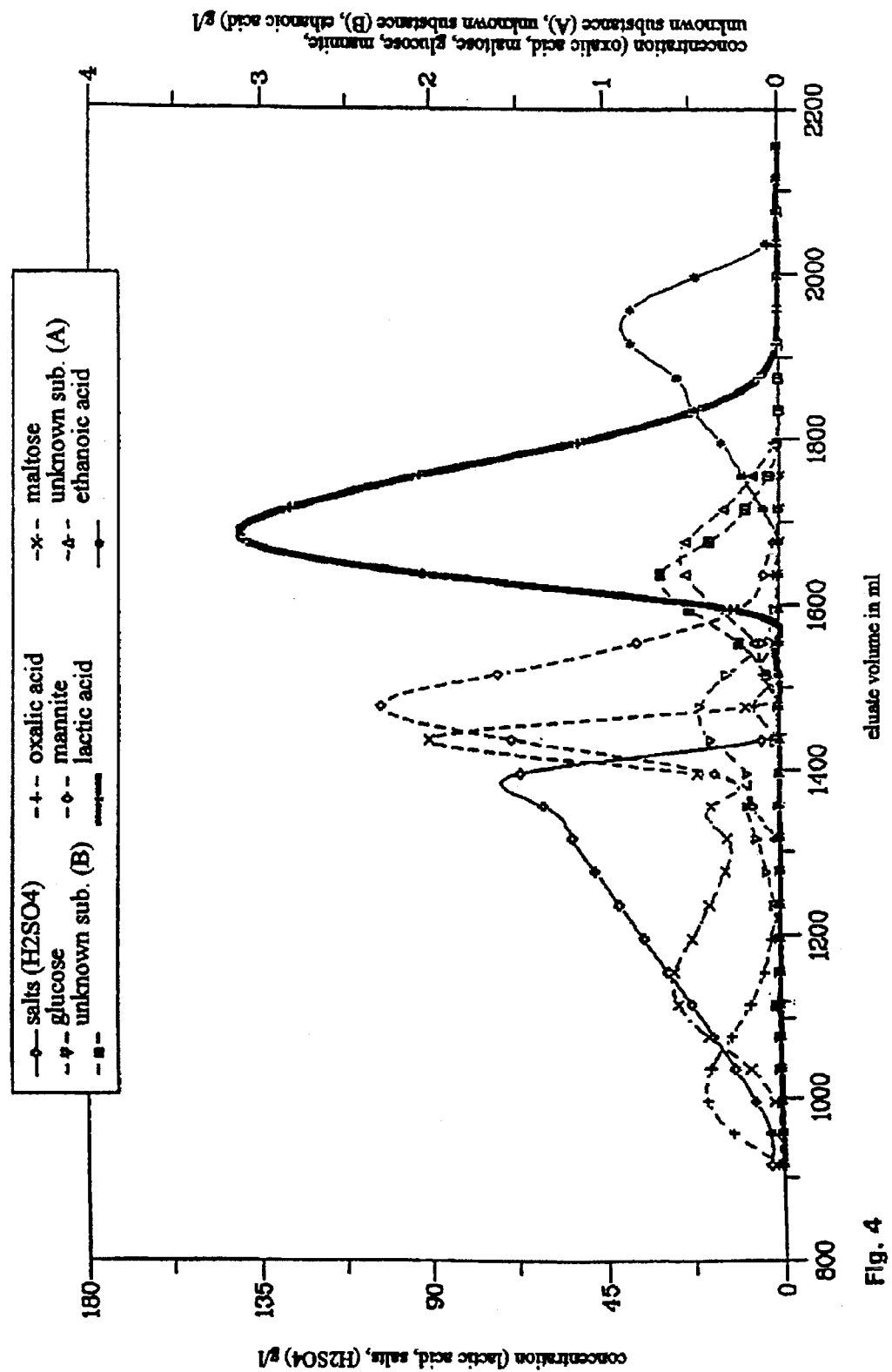

The procedure was identical to Example 3, except that 60 ml of "feed" solution 1 was applied to the resin. The chromatogram of this separation is shown in FIG. 4.

EXAMPLE 5

The procedure was identical to Example 4, except that the chromatography installation was supplemented by a "preliminary column". At a diameter of 2.5 cm and a resin bed height of 80 cm, this "preliminary column" had a resin bed volume of approximately 400 cm$^3$. The "preliminary column" was packed with the weakly acid cation exchanger Dowex MWC-1 and brought to H$^+$ form by a 1N H$_2$SO$_4$. The "preliminary column" was maintained at a constant temperature of 75° C. by a circulating thermostat. Next, 60 ml of "feed" solution 1 were applied to the "preliminary column" and elution was carried out with preheated (70° C.) deionized water with a flow rate of 9 ml/min (2.8 ml/min*cm$^2$). The chromatogram of this separation is shown in FIG. 5.

The lactic acid fraction was subjected to the so-called "heat" test. For this purpose, a sample of this fraction was heated for one hour at 200° C. in a glycerin bath in a pressure-proof sealable tube. Extinction before and after heating was determined at 420 nm (layer thickness 1 cm).

TABLE 3

| feature | extinction |
|---|---|
| "feed" solution 1 | 0.412 |
| sample before heating | 0.006 |
| sample after heating | 0.014 |

EXAMPLE 6

The procedure was identical to Example 5, except that the "preliminary column" was packed with the strongly acidic cation exchanger Lewatit MDS 1368 and brought to H$^+$ form with H$_2$SO$_4$ (2N) The chromatogram of this separation is shown in FIG. 6.

EXAMPLE 7

Figure 7:
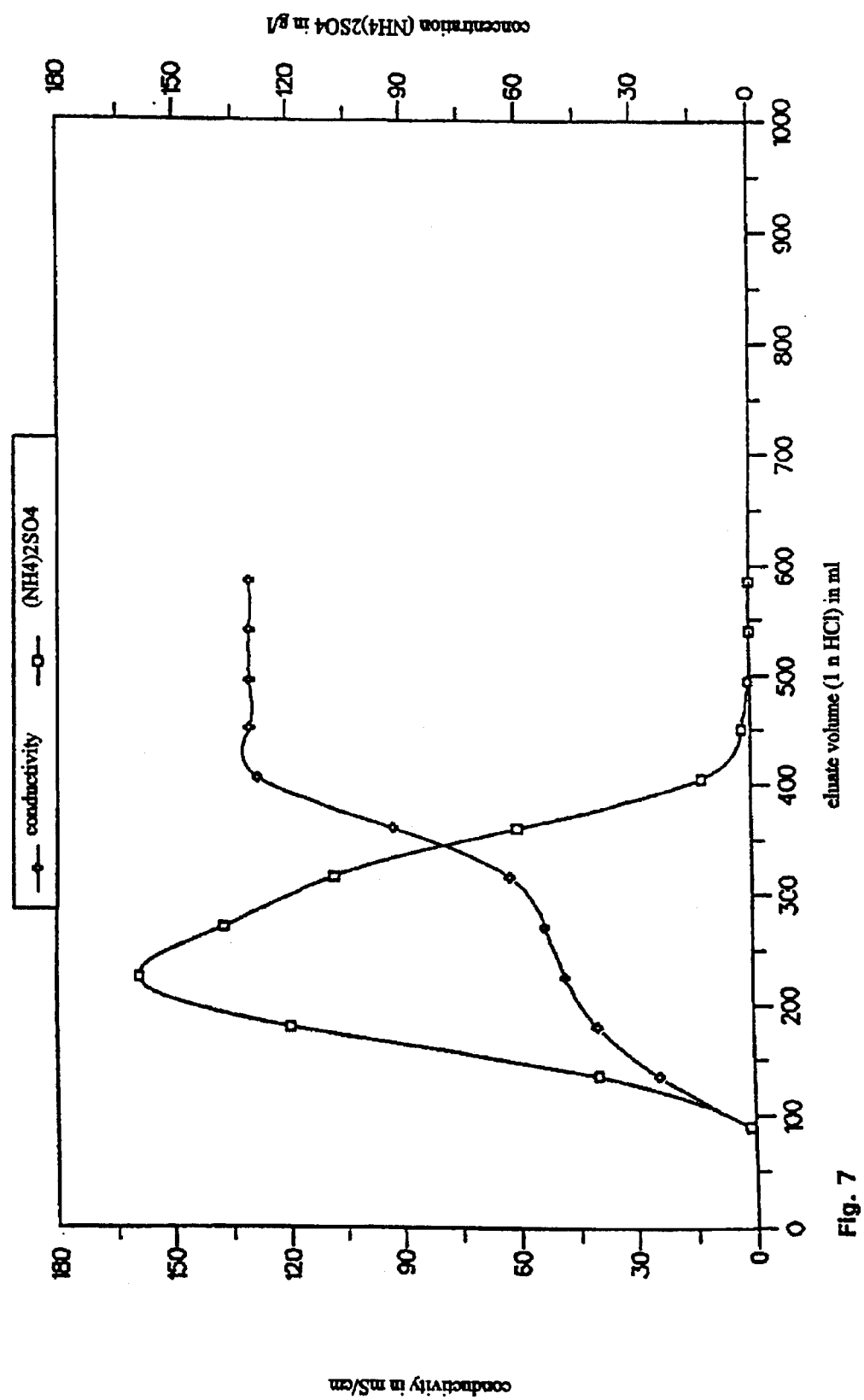
FIG. 7 is a graphical illustration of regenration of a weakly acidic cation exchanger.

The weakly acidic cation exchanger Dowex MWC-1 in the "preliminary column" which was loaded with NH$_4^+$ ions in Example 5 was regenerated with H$_2$SO$_4$ (1N). The solution exiting from the "preliminary column" ran through a conductivity measurement cell and was then collected in a fraction collector. The concentration of ammonium sulfate in the individual fractions was determined by adding concentrated NaOH and by subsequent steam distillation with the Büchi "distiller unit". The results of this test are shown in FIG. 7.

EXAMPLE 8

Figure 8:
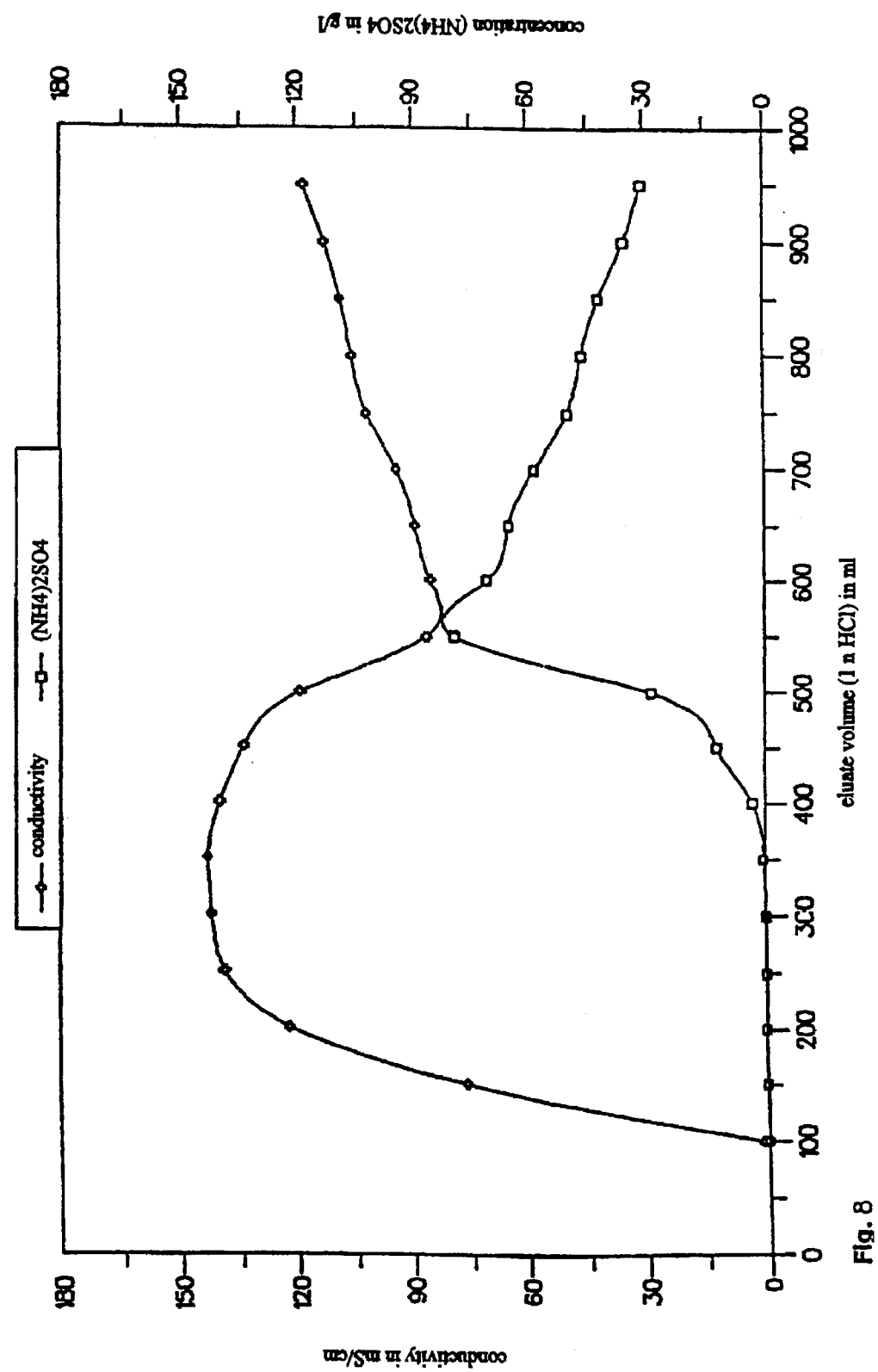
FIG. 8 is a graphical illustration of regenration of a strongly acidic cation exchanger.

The procedure was identical to Example 7, except that the strongly acidic cation exchanger Lewatit MDS 1368 which was loaded with NH$_4^+$ ions in Example 6 was regenerated in the "preliminary column" with H$_2$SO$_4$ (1N) The results of this test are shown in FIG. 8.

We claim:

1. Process for the separation and purification of lactic acid from salt-containing and carbohydrate-containing substrates from a fermentation solution from which coarsely dispersed and lipophilic impurities have been removed, said separation and purification process comprising the steps of:
   a) converting the salts which may be present in the fermentation solution, principally the salt of lactic acid, into free acids by means of genuine ion exchange in one or more "preliminary columns", and
   b) separating the free lactic acid from the rest of the acids, carbohydrates and other impurities present in the fermentation solution by chromatography at strongly acidic ion exchangers in one or more "separation columns".

2. Process according to claim 1, wherein the fermentation solution from which the lactic acid is separated has a pH greater than 5.0.

3. Process according to claim 1 wherein the resin located in one or more "preliminary columns" is a cation exchanger.

4. Process according to claim 3 wherein the temperature of the "preliminary column" is at least 50° C.

5. Process according to claim 4 wherein the temperature of the "preliminary column" is 70°–80° C.

6. Process according to claim 3 wherein the cation exchanger is a weakly acidic cation exchanger in H$^+$ form.

7. Process according to claim 1, wherein the strongly acidic cation exchanger found in one or more "separation columns" is present in H$^+$ form.

8. Process according to claim 1, wherein the decationized fermentation solution, upon contact with the strongly acidic cation exchanger, is divided into a raffinate fraction I (initial fraction) containing the components without a lactic acid content, a product fraction containing lactic acid, and a raffinate fraction II (final fraction) containing primarily ethanoic acid.

9. Process according to claim 8 wherein the elution temperature lies between room temperature and the stability threshold temperature of the resins employed.

10. Process according to claim 9, wherein the diluted salt solution occurring in the regeneration of the resins in the preliminary columns is separated into the corresponding acids and bases by salt-hydrolyzing electrodialysis and fed back to the process.

11. Process according to claim 9 wherein the elution temperature lies between 50° C. and 65° C.

12. Process according to claim 1 wherein pure water is used as eluting agent for washing the individual fractions out of the separation columns.

13. Process according to claim 12 wherein the pure water is deionized.

14. Process according to claim 1 wherein only the weakly acidic cation exchanger located in the "preliminary columns" is regenerated with a diluted strong mineral acid after being completely loaded by the cations of the fermentation solution.

15. Process according to claim 14 wherein the diluted strong mineral acid is a 1–2N sulfuric acid.

* * * * *